United States Patent
Ayyagari et al.

(10) Patent No.: US 6,423,820 B1
(45) Date of Patent: Jul. 23, 2002

(54) PROCESS FOR PURIFYING AND REUSING SOLVENT USED TO REMOVE EXTRACTABLES

(75) Inventors: Madhu Ayyagari, Fairport; Erik M. Indra, Webster; Mahendra P. Nandu, Rochester, all of NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 19 days.

(21) Appl. No.: 09/667,902

(22) Filed: Sep. 22, 2000

Related U.S. Application Data

(60) Provisional application No. 60/155,967, filed on Sep. 24, 1999.

(51) Int. Cl.$^7$ ................................................. C08J 3/00
(52) U.S. Cl. ....................................................... 528/491
(58) Field of Search ........................................ 528/491

(56) References Cited

U.S. PATENT DOCUMENTS

| | | | |
|---|---|---|---|
| 3,408,429 A | 10/1968 | Wichterle | |
| 3,660,545 A | 5/1972 | Wichterle | 264/1 |
| 3,970,605 A * | 7/1976 | Wentworth | 260/79.3 |
| 4,028,337 A * | 6/1977 | Starnes, Jr. | 260/45.75 |
| 4,095,020 A * | 6/1978 | Prest, Jr. et al. | 528/494 |
| 4,113,224 A | 9/1978 | Clark et al. | 249/105 |
| 4,128,405 A * | 12/1978 | Frohreich et al. | 55/59 |
| 4,153,641 A | 5/1979 | Deichert et al. | 260/827 |
| 4,197,266 A | 4/1980 | Clark et al. | 264/1 |
| 4,502,957 A | 3/1985 | Jehle et al. | 210/690 |
| 4,555,732 A | 11/1985 | Tuhro | 358/213 |
| 4,581,431 A * | 4/1986 | Yamazaki et al. | 528/494 |
| 4,740,533 A | 4/1988 | Su et al. | 523/106 |
| 4,749,496 A | 6/1988 | Reischl | 210/692 |
| 4,795,516 A * | 1/1989 | Strand | 156/235 |
| 4,869,909 A * | 9/1989 | Takahashi | 424/486 |
| 4,893,629 A * | 1/1990 | Lewis | 128/660.07 |
| 4,950,816 A * | 8/1990 | Tung | 570/179 |
| 5,034,461 A | 7/1991 | Lai et al. | 525/100 |
| 5,070,215 A | 12/1991 | Bambury et al. | 556/418 |
| 5,260,000 A | 11/1993 | Nandu et al. | 264/2.1 |
| 5,370,891 A | 12/1994 | Fillipova | 426/422 |
| 5,587,449 A * | 12/1996 | Fleischer et al. | 528/232 |
| 5,607,518 A | 3/1997 | Hoffman et al. | 134/31 |
| 5,770,778 A | 6/1998 | Naujokas | 568/872 |
| 5,789,461 A | 8/1998 | Nicolson et al. | 523/106 |
| 5,936,007 A * | 8/1999 | Ebert et al. | 523/136 |
| 6,160,086 A * | 12/2000 | Holm et al. | 528/491 |
| 6,221,103 B1 * | 4/2001 | Melvin | 623/3.1 |

FOREIGN PATENT DOCUMENTS

| | | | | |
|---|---|---|---|---|
| EP | WO 95/20476 | 8/1995 | ........... | B29C/37/00 |
| EP | WO 98/07554 | 12/1999 | ........... | A61L/27/00 |
| GB | 649583 | 1/1951 | ........... | 46/91 |
| GB | 2 226 554 A | 12/1988 | ........... | C07C/17/38 |

* cited by examiner

*Primary Examiner*—Paul R. Michl
(74) *Attorney, Agent, or Firm*—John E. Thomas

(57) ABSTRACT

A process for treating biomedical devices, especially contact lenses, involves contacting polymeric devices containing extractables with a solvent that dissolves and thereby removes the extractables from the device, treating the solvent to remove extractables from the solvent, thereby purifying the solvent, and using the purified solvent to remove additional extractables from polymeric devices.

12 Claims, 2 Drawing Sheets

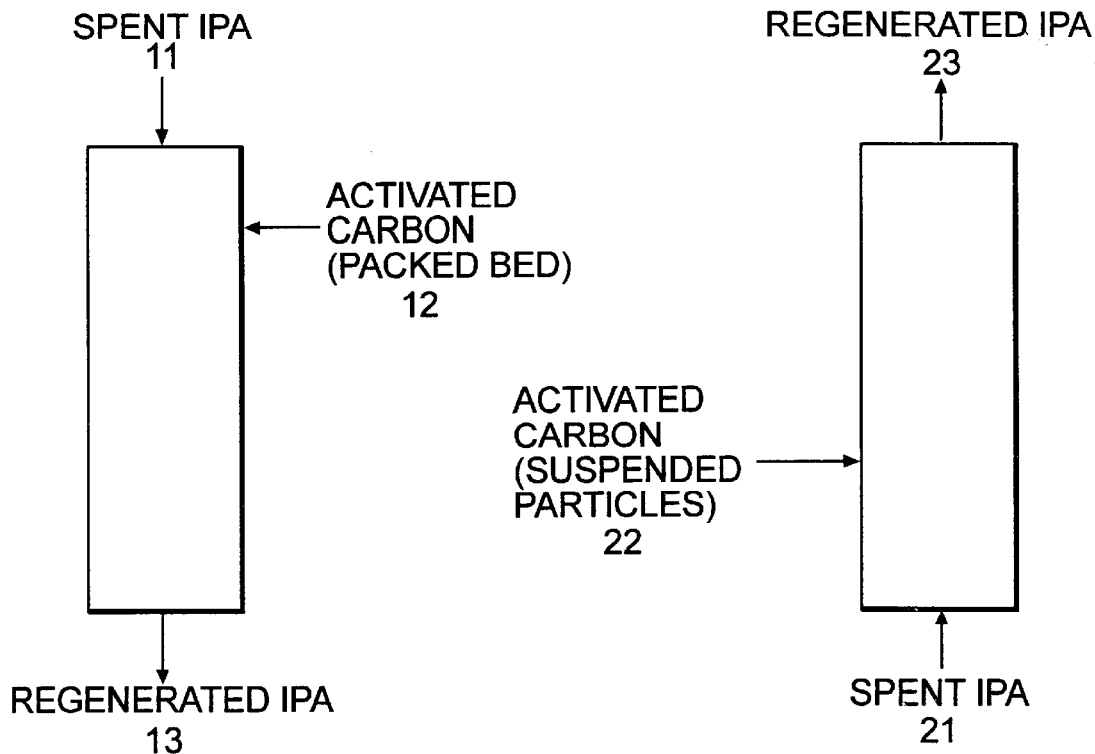
FIG. 1
FIG. 2
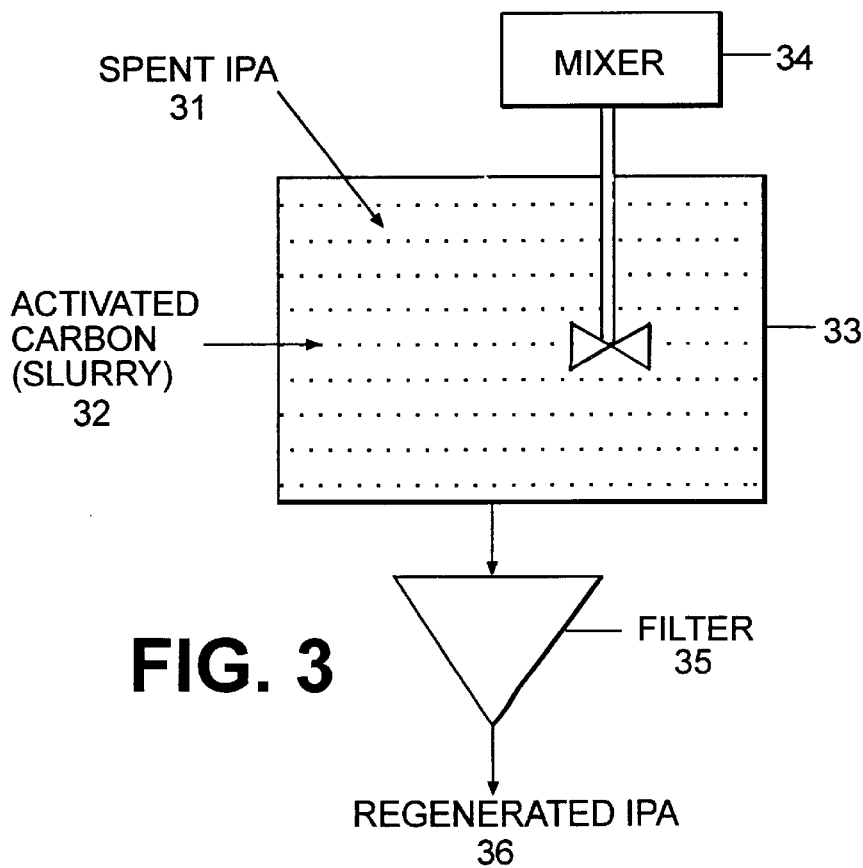
FIG. 3

PROCESS FOR PURIFYING AND REUSING SOLVENT USED TO REMOVE EXTRACTABLES

This application claims priority under 35 USC 119(e) of prior provisional application 60/155,967, filed Sep. 24, 1999.

FIELD OF THE INVENTION

The present invention relates to a process for purifying and reusing solvent used to remove extractables from polymeric biomedical devices, particularly ophthalmic devices including contact lenses, intraocular lenses and ophthalmic implants.

BACKGROUND OF THE INVENTION

Hydrogels represent a desirable class of materials for the manufacture of various biomedical devices, including contact lenses. A hydrogel is a hydrated cross-linked polymeric system that contains water in an equilibrium state. Hydrogel lenses offer relatively high oxygen permeability as well as desirable biocompatibility and comfort.

In a typical process for the manufacture of hydrogel polymeric contact lenses, a composition containing a diluent and suitable monomers is charged to a mold and cured. The molded lens can be subjected to machining operations such as lathe cutting, buffing, and polishing and further subjected to extraction, hydration, and sterilization procedures.

Generally, in the manufacture of contact lenses, some of the monomer mix components are not fully polymerized. The incompletely polymerized material from the polymerization process may affect optical clarity or be harmful to the eye. Residual material, which may be either hydrophilic or hydrophobic, include solvents, unreacted monomers, or low molecular weight oligomers. Hydrophilic residual materials can be extracted by water; hydrophobic residual components, referred to herein as "extractables," are typically removed by extraction with water-miscible organic solvents, in particular, alcohols such as isopropanol. Following the alcohol extraction process, the lens needs to be hydrated by treatment with water before being sterilized by, for example, autoclaving in buffered saline. A typical extraction procedure is described in the Examples of U.S. Pat. No. 5,260,000 and Example B-11 of U.S. Pat. No. 5,789,461, in which contact lenses are removed from the molds in which they were formed and extracted with isopropanol. As an alternative extraction process, U.S. Pat. No. 5,607,518, and PCT Publications WO 95/20476 and WO 98/07554, disclose a method of contacting a contact lens with carbon dioxide, which may be mixed with isopropanol, to extract residual material from a contact lens.

A drawback of extracting with isopropanol for commercial scale manufacturing is that the replacement and disposal of relatively large volumes of spent solvent may be required, which is undesirable both economically and environmentally. The present invention provides for reducing the amount of spent extraction solvent in the manufacture of biomedical devices.

SUMMARY OF THE INVENTION

This invention provides an improved process for producing biomedical devices, particularly ophthalmic biomedical devices, wherein polymeric devices containing extractables are contacted with a solvent able to dissolve the extractables from the devices, thereby removing the extractables; treating the solvent containing the extractables under conditions effective to remove extractables from the solvent, thereby purifying it; and using the purified solvent to remove additional extractables. The purified solvent may be used to remove extractables from other polymeric devices, or the purified solvent may be used in a subsequent batch treatment of the same polymeric devices to remove additional extractables therefrom.

BRIEF DESCRIPTION OF THE DRAWINGS

FIGS. 1 and 2 are schematic representations of the process of the present invention using, respectively, a packed-bed column and a fluidized-bed column.

FIG. 3 is a schematic representation of the process of the present invention using a suspension of adsorbing agent in a batch process.

DETAILED DESCRIPTION OF VARIOUS PREFERRED EMBODIMENTS

Figures 4, 5:
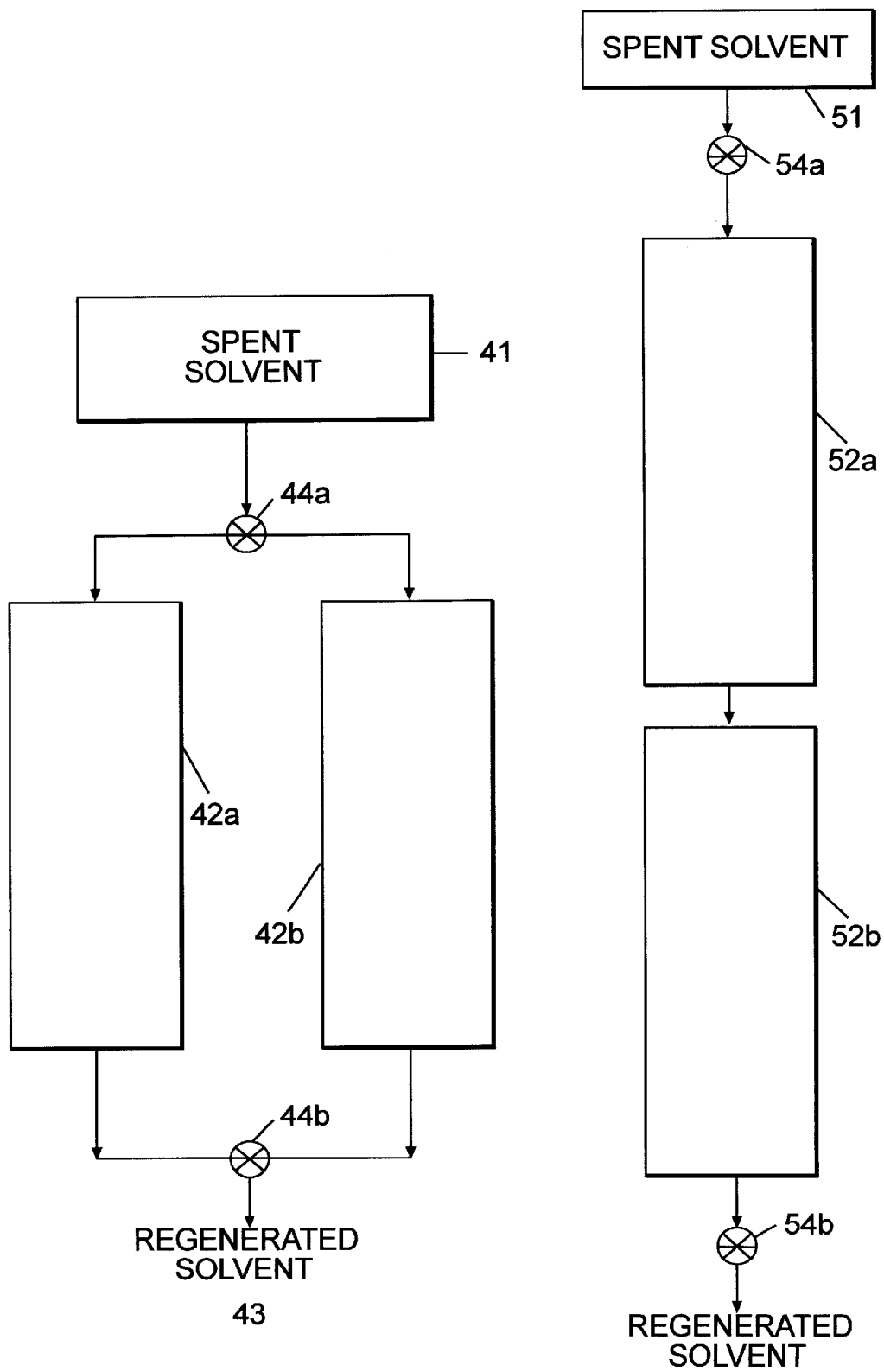
FIGS. 4 and 5 are schematic representations of the process of the present invention using two columns in, respectively, a parallel array and a series array.

The present invention provides a method for removing extractables from biomedical devices, especially ophthalmic biomedical devices. The term "biomedical device" means a device intended for direct contact with living tissue. The term "ophthalmic biomedical device" means a device intended for direct contact with ophthalmic tissue, including contact lenses, intraocular lenses and ophthalmic implants. In the following description, the process is discussed with reference to hydrogel contact lenses, an especially preferred embodiment of this invention.

Hydrogel lenses are generally formed of a copolymer of at least one hydrophilic monomer and a cross-linking monomer. The hydrophilicity is due to the presence of hydrophilic groups such as, for example, hydroxy, carboxylic acid, amide and sulfonic acid. The swollen equilibrated state results from a balance between the osmotic driving forces that cause the water to enter the hydrophilic polymer and the forces exerted by the polymer chains in resisting expansion. Lenses in this class are generally formed of a copolymer of at least one hydrophilic monomer and a cross-linking monomer. Hydrophilic monomers include: unsaturated carboxylic acids such as methacrylic acid and acrylic acid; (meth) acrylic substituted alcohols or glycols such as 2-hydroxyethyl methacrylate, 2-hydroxyethyl acrylate, and glyceryl methacrylate; vinyl lactams such as N-vinyl-2-pyrrolidone; and acrylamides such as methacrylamide and N,N dimethylacrylamide. Further examples of such hydrophilic monomers can be found in U.S. Pat. Nos. 4,153,641; 4,740,533; 5,034,461; and 5,070,215.

The cross-linking monomer may be material having multiple polymerizable functionalities, preferably vinyl functionalities. Representative cross linking monomers include: divinylbenzene, allyl methacrylate, ethylene glycol dimethacrylate, tetraethyleneglycol dimethacrylate, polyethyleneglycol dimethacrylate, and vinyl carbonate derivatives of the glycol dimethacrylates. In the case of silicone hydrogel contact lenses, the copolymeric material further includes at least one silicone-containing monomer.

An organic diluent is included in the initial monomeric mixture. As used herein, the term "organic diluent" encompasses organic compounds that minimize incompatibility of the components in the initial monomeric mixture and are substantially unreactive with the components in the initial mixture. Additionally, the organic diluent serves to minimize phase separation of polymerized products produced by polymerization of the monomeric mixture. Also, the organic diluent will generally lower the glass transition temperature of the reacting polymeric mixture, which allows for a more efficient curing process and ultimately results in a more uniformly polymerized product. Uniformity of the initial monomeric mixture and the polymerized product are of particular concern for silicone hydrogels primarily due to the inclusion of silicone-containing monomers.

Contemplated organic diluents include: monohydric alcohols, with $C_6$–$C_{10}$ straight-chained aliphatic monohydric alcohols being especially preferred; diols such as ethylene glycol; polyols such as glycerin; ethers such as diethylene glycol monoethyl ether; ketones such as methyl ethyl ketone; esters such as methyl heptanoate; and hydrocarbons such as toluene. Preferably, the organic diluent is sufficiently volatile to facilitate its removal from a cured article by evaporation at or near ambient pressure.

Various processes are known for curing a monomeric mixture in the production of contact lenses including spincasting and static casting. Spincasting methods are disclosed in U.S. Pat. Nos. 3,408,429 and 3,660,545, and static casting methods are disclosed in U.S. Pat. Nos. 4,113,224 and 4,197,266, the disclosures of all of which are incorporated herein by reference. Curing of the monomeric mixture may be followed by a machining operation in order to provide a contact lens having a desired final configuration.

According to several known techniques for manufacturing contact lenses, the casting process may yield a shaped article having the desired posterior and anterior lens surfaces. For example, in static casting processes, a monomeric mixture can be charged to a mold comprising a first mold section including a surface for forming a desired anterior lens surface and a second mold section including a surface for forming a desired posterior lens surface. In spincasting processes, the monomeric mixture can be charged to an open mold having a surface for forming a desired anterior lens surface, and a desired posterior lens surface is formed from rotation of the mold. However, machining operations subsequent to the curing of the article may still be necessary to provide a contact lens more suitable for placement on the eye. Such machining operations including lathe cutting the lens to obtain a desired lens edge, buffing the lens edge, or polishing the lens edge or surface.

In other known manufacturing techniques, the casting process may yield a shaped article that does not have the desired anterior and/or posterior lens surfaces. Accordingly, the casting process is followed by a machining operation to form a desired lens surface. As an example, U.S. Pat. No. 4,555,732, the disclosure of which is incorporated herein by reference, describes a process where an excess of a monomeric mixture is curved by spincasting in a mold to form a shaped article having an anterior lens surface and a relatively large thickness; the posterior surface of the cured spincast article is subsequently lathe cut to provide a contact lens having the desired thickness and posterior lens surface. Further machining operations such as the previously described edge finishing operations may follow the lathe cutting of the lens surface.

Removal of extractable components from polymeric contact lenses, is typically carried out by contacting the lenses with an extraction solvent for a period of time sufficient to ensure substantially complete removal of the components. For example, a batch of contact lenses is immersed in a bath of isopropanol and held for several hours to effect removal of extractables such as monomers and oligomers from the lenses. The lenses are removed, and a new batch is immersed in the bath. After several hours holding, this batch is removed, and the process is repeated. Thus, the isopropanol is reused, several thousand contact lenses being extracted with a given quantity of isopropanol before it is replaced with fresh solvent.

In the isopropanol bath, the concentration of extractables builds up as lens extraction proceeds and results in decreased efficiency in the removal of extractable material from the lenses. Thus, even though all the lenses extracted by a bath of isopropanol may meet finished product specifications, there is a trend of lenses extracted near the end of the solvent bath lifetime containing higher levels of residual extractables than those treated earlier in its lifetime. Maintaining uniform extraction efficiency during the lifetime of the solvent bath is desirable and could obviously be achieved by lowering the number of lenses treated by a given quantity of solvent, but this would be undesirable from both an economic and an environmental standpoint. Alternatively, extraction efficiency can be maintained by continuously replenishing the solvent; however, this approach may result in generation of large amounts of contaminated solvent requiring disposal.

The process of the present invention provides a desirable way of extending the useful lifetime of a solvent bath used to remove extractables from polymeric contact lenses. Consequently, the volumes of spent solvent requiring disposal are substantially reduced.

FIG. 1 schematically depicts the regeneration of a spent solvent 11 such as isopropanol from a lens extraction procedure by passing solvent 11, which contains extractable materials removed from polymeric contact lenses (not shown), through a packed-bed column 12 of an adsorbing agent, for example, activated carbon. The adsorbing agent removes the extractables from solvent 11, resulting in a purified solvent 13 that is useful for efficiently extracting an additional quantity of contact lenses (not shown), or for extracting additional extractables from the same polymeric contact lenses.

FIG. 2 is a schematic illustration similar to FIG. 1 but depicting a fluidized-bed column 22 of an adsorbing agent for converting spent solvent 21 to purified solvent 23. A fluidized-bed 22 has the advantage of reduced pressure drop compared with a packed-bed 12.

FIG. 3 is a schematic illustration of a batch technique for purifying a spent extractable-laden solvent 31 by contacting it with suspended adsorbing agent 32 in a vessel 33 equipped with a stirrer 34. A filter 35 is used to remove adsorbing agent 32 from purified solvent 36.

Suitable adsorbing agents for use in columns 12 and 22 of FIGS. 1 and 2, respectively, or suspended in vessel 33 of FIG. 3 include activated carbon, hydrophobic molecular sieves, activated carbon molecular sieves, silica, and alumina. If desired, a mixture of adsorbing agents can be employed in the columns.

In accordance with present invention, activated carbon is a preferred adsorbing agent. U.S. Pat. No. 5,370,891 to Fillipova, the disclosure of which is incorporated herein by reference, describes the purification of ethyl alcohol for vodka by passing an ethyl-alcohol mixture through three layers of activated charcoal adsorber of increasing surface activity. The activity of the adsorbent is said to be restored after use by flowing a stream of heated dry air through the activated charcoal layers.

U.S. Pat. No. 5,770,778 to Naujokas, the disclosure of which is incorporated herein by reference, describes a process for purifying ethylene glycol recovered from scrap polyester by contacting the recovered glycol with, in either order, a first adsorbent that has a high affinity for polar contaminants and a second adsorbent that has a high affinity for non-polar contaminants. Examples of adsorbents with high affinity for polar contaminants include alumina and silica; among those with high affinity for non-polar contaminants are activated carbon and hydrophobic and activated carbon molecular sieves.

FIG. 4 schematically depicts the purification of a contaminated solvent 41 to purified solvent 43 by passing the spent solvent through two adsorbing columns 42a and 42b, shown arranged in a parallel configuration. This arrangement would be useful for increasing throughput in the solvent purification step. The adsorbing agent employed in columns 42a and 42b can be a single material or a mixture of adsorbents. The flow of solvent through columns 42a and 42b can be regulated by the use of valves 44a and 44b.

FIG. 5 shows a similar procedure for purifying a contaminated solvent 51 to a purified solvent 53, using two adsorbent columns 52a and 52b that are, in this instance, arranged in series. This arrangement could be beneficial for improving the completeness of extractables removal from the spent solvent. The adsorbing agent contained in column 52a can be the same or different from that used in column 52b. Again, valves 54a and 54b can be used to control fluid flow.

The process of the present invention is illustrated by the following examples using, in each instance, small samples taken from 55 gallons of isopropyl alcohol that had been used to extract about 6000 polymeric contact lenses:

(A) A 100-mL sample of the described spent isopropanol is run through a column, one inch in diameter and two feet in height, packed with about 10 grams of 100 mesh carbon. Gas chromatography (GC) and size-exclusion chromatography (SEC) are used before and after passage of the sample through the packed carbon column to measure the removal of two major components: a monomeric precursor of the lens polymer and a related low molecular-weight compound. The described treatment results in removal of 93.45% of the total of the two monitored extractable components.

(B) A 25-mL sample of spent isopropanol is stirred for about 16 hours at ambient temperature with about 5 grams of 100 mesh activated carbon, then separated from the adsorbent by filtration. This treatment results in the removal of 93.20% of the total of the two monitored extractable components from the solvent.

Having thus described the preferred embodiment of the invention, those skilled in the art will appreciate that various modifications, additions, and changes may be made thereto without departing from the spirit and scope of the invention, as set forth in the following claims.

What is claimed:

1. A process for producing a polymeric contact lens, comprising:

contacting a polymeric contact lens that contains extractables with a solvent effective for dissolving said extractables, thereby removing said extractables from said contact lens;

treating the solvent containing said extractables under conditions effective for removing the extractables from the solvent, thereby purifying said solvent; and using the purified solvent for removing additional extractables from polymeric contact lenses.

2. The process of claim 1 wherein the purified solvent is used for removing additional extractables from said contact lens.

3. The process of claim 1 wherein the purified solvent is used for removing extractables from other polymeric contact lenses.

4. The process of claim 1 wherein treating the extractables-containing solvent comprises contacting the solvent with an adsorbing agent effective for adsorbing said extractables.

5. The process of claim 4 wherein the adsorbing agent is included in at least one column, and the extractables-containing solvent flows through said column.

6. The process of claim 5 wherein said column is a packed-bed column or a fluidized-bed column.

7. The process of claim 5 wherein said adsorbing agent is included in a plurality of columns, disposed in parallel array or a series array.

8. The process of claim 4 wherein said adsorbing agent is suspended in the extractables-containing solvent.

9. The process of claim 8 wherein said adsorbing agent and said extractables-containing solvent are contained in a vessel provided with an agitator for stirring said adsorbing agent and said solvent, and a filter for separating said adsorbing agent from said solvent.

10. The process of claim 4 wherein said adsorbing agent is selected from the group consisting of activated carbon, hydrophobic molecular sieves, activated carbon molecular sieves, silica, and alumina.

11. The process of claim 10 wherein said adsorbing agent is activated carbon.

12. The process of claim 1 wherein said solvent comprises isopropanol.

* * * * *